United States Patent [19]
Takano et al.

[11] Patent Number: 5,170,793
[45] Date of Patent: Dec. 15, 1992

[54] ULTRASONIC PROBE

[75] Inventors: Masayuki Takano; Hiroshi Sasaki, both of Ootawara, Japan

[73] Assignee: Kabushiki Kaisha Toshiba, Kawasaki, Japan

[21] Appl. No.: 651,991

[22] Filed: Feb. 7, 1991

[30] Foreign Application Priority Data

Feb. 7, 1990 [JP] Japan .................................. 2-28759

[51] Int. Cl.⁵ .............................................. A61B 8/12
[52] U.S. Cl. ........................ 128/662.06; 128/663.01; 128/660.09
[58] Field of Search ....................... 128/662.03, 662.05, 128/662.06, 663.01, 660.09

[56] References Cited

U.S. PATENT DOCUMENTS

| | | | |
|---|---|---|---|
| 4,732,156 | 3/1988 | Nakamura | 128/662.06 |
| 4,899,757 | 2/1990 | Pope, Jr. et al. | 128/663.01 |
| 5,000,185 | 3/1991 | Yock | 128/662.03 |
| 5,024,234 | 6/1991 | Leary et al. | 128/662.06 |
| 5,029,588 | 7/1991 | Yock et al. | 128/662.06 |

Primary Examiner—Francis Jaworski
Assistant Examiner—George Manuel
Attorney, Agent, or Firm—Oblon, Spivak, McClelland, Maier & Neustadt

[57] ABSTRACT

An ultrasonic probe including a rotary transmission shaft to be rotated by a driver connected thereto, in which an oscillator is arranged in opposition to one end of the transmission shaft for emitting a ultrasonic wave, and a scanner such as a mirror is mounted to the one end of the rotary transmission shaft for reflecting the ultrasonic wave emitted by the oscillator to carry out an ultrasonic wave scanning. The rotary transmission shaft includes a first shaft having a first diameter, connected to the scanner, and a second shaft having a second diameter, connected to the driver with the first diameter being smaller than the second diameter. The oscillator as the scanner may be directly mounted to the end of the transmission shaft.

20 Claims, 4 Drawing Sheets

ULTRASONIC PROBE

BACKGROUND OF THE INVENTION

1. Field of the Invention

The present invention relates to an ultrasonic probe to be inserted into a narrow portion such as a hole, a hollow or the like, and particularly inserted into a blood vessel of a heart for carrying out a mechanical radial or sector scanning within the blood vessel.

2. Description of the Background Art

In FIG. 1, there is shown a conventional ultrasonic probe 1 of a mechanical radial scanning type. In the probe 1, an oscillator 2 having a diameter of approximately 2 mm is arranged in a tip of a tubular case 5, and a mirror 3 is arranged in opposition to the oscillator 2 within the tubular case 5 and is surrounded by a ultrasonic wave propagation material 8 such as water or a physiological saline solution. The mirror 3 is secured to a shaft 3a which is connected to a rotary transmission shaft 4 having an outer diameter of approximately several mm, which is composed of a tubular coil or coil spring 4a made of a steel wire. In the tubular case 5, the shaft 3a of the mirror 3 is supported by a bearing 6 mounted on the case 5 through the rotary transmission shaft 4. The rotary transmission shaft 4 is connected to a driver such as a motor M or the like. When the motor M is driven, a rotary driving force in an X-direction is transmitted to the mirror 3 through the rotary transmission shaft 4 to rotate the mirror 3 in a Y-direction, and the mirror reflects a ultrasonic wave radiated by the oscillator 2 to carry out a ultrasonic wave scanning in a radial plane F.

In FIG. 2, there is shown another conventional ultrasonic probe 10 of a mechanical radial scanning type. In the probe 10, an oscillator 12 having a diameter of approximately 2 mm is arranged in a tip of a tubular case 15, and a mirror 13 is arranged in opposition to the oscillator 12 within the tubular case 15. The mirror 13 is secured to a shaft 13b having a hollow 13a in its end, and a rotary transmission shaft 14 composed of a steel wire having a diameter of approximately 1 mm is connected to the shaft 13b by inserting one end of the rotary transmission shaft 14 in the hollow 13a of the shaft 13b. In the tubular case 15, the shaft 13b of the mirror 3 is supported by a bearing 16 mounted on the case 15. The rotary transmission shaft 14 is connected to the motor M to function in the same manner as the rotary transmission shaft 4 shown in FIG. 1.

When the above described probe 1 or 10 is inserted into blood vessels such as aorta $B_1$ having a diameter of approximately 20 to 30 mm, coronary artery (chief trunk portion) $B_2$ having a diameter of approximately 3 to 5 mm and ramus circumflexus $B_3$ having a diameter of less than 2 mm or ramus descendens $B_4$ having a diameter of less than 2 mm of a heart H of an adult, as shown in FIG. 3, in order to carry out a ultrasonic wave scanning in a radial plane F or the internal surfaces of the blood vessels, the probe 1 or 10 is first inserted from its oscillator 2 or 12 into the aorta $B_1$, and is then bent at an angle of approximately 90 degree to go into the coronary artery $B_2$. Then, the oscillator 2 or 12 of the probe 1 or 10 is bent in an inclined direction to be inserted into the fine ramus circumflexus $B_3$ or ramus descendens $B_4$. Then, by driving the motor M, the mirror 3 or 13 is rotated to perform a mechanical radial scanning in the ramus circumflexus $B_3$ or ramus descendens $B_4$. A ultrasonic probe capable of clinically performing a ultrasonic wave scanning in a radial plane within a fine blood vessel such as the ramus circumflexus $B_3$ or ramus descendens $B_4$ has been demanded.

However, in one conventional ultrasonic probe 1 shown in FIG. 1, since, even when an oscillator 2 having a diameter of less than 2 mm is used, the diameter of the rotary transmission shaft 4 is big such as several mm over its entire length, it is impossible to insert the probe 1 into a fine blood vessel such as the ramus circumflexus or ramus descendens.

Further, in another conventional ultrasonic probe 10 shown in FIG. 2, since the rotary transmission shaft 14 is composed of a linear steel wire, when the transmission shaft 14 is largely bent, one side having a small curvature of the transmission shaft 14 receives a compression force and another side having a large curvature receives an extension force. Accordingly, even when the motor M is rotated 90 degree, the mirror 13 connected to the transmission shaft 14 often rotates only 30 degrees due to such a stress given to the transmission shaft 14, that is, the rotating force of the motor M can not be smoothly transmitted to the mirror 13. Hence, an uneven or irregular rotation of the mirror 13 is caused, and a good ultrasonic wave image can not be obtained.

SUMMARY OF THE INVENTION

Accordingly, it is an object of the present invention to provide an ultrasonic probe in view of the aforementioned defects and disadvantages of the prior art, which is capable of inserting into a fine portion such as a fine blood vessel or the like and preventing an irregular rotation of a mirror to obtain a good ultrasonic wave image.

In accordance with one aspect of the present invention, there is provided an ultrasonic probe, comprising a rotary transmission shaft to be rotated by a driver connected thereto, an oscillator arranged in opposition to one end of the transmission shaft for emitting a ultrasonic wave, and scanning means mounted to the one end of the rotary transmission shaft for reflecting the ultrasonic wave emitted by the oscillator to carry out an ultrasonic wave scanning, the rotary transmission shaft including a first shaft having a first diameter, connected to the scanning means, and a second shaft having a second diameter, connected to the driver, the first diameter being smaller than the second diameter.

In accordance with another aspect of the present invention, there is provided an ultrasonic probe, comprising a rotary transmission shaft to be rotated by a driver connected thereto, and scanning means mounted to the one end of the rotary transmission shaft for emitting a ultrasonic wave to carry out an ultrasonic wave scanning, the rotary transmission shaft including a first shaft having a first diameter, connected to the scanning means, and a second shaft having a second diameter, connected to the driver, the first diameter being smaller than the second diameter.

BRIEF DESCRIPTION OF THE DRAWINGS

The above and other objects, features and advantages of the present invention will more fully appear from the following description of the preferred embodiments with reference to the accompanying drawings, in which.

DESCRIPTION OF THE PREFERRED EMBODIMENTS

Figure 4:
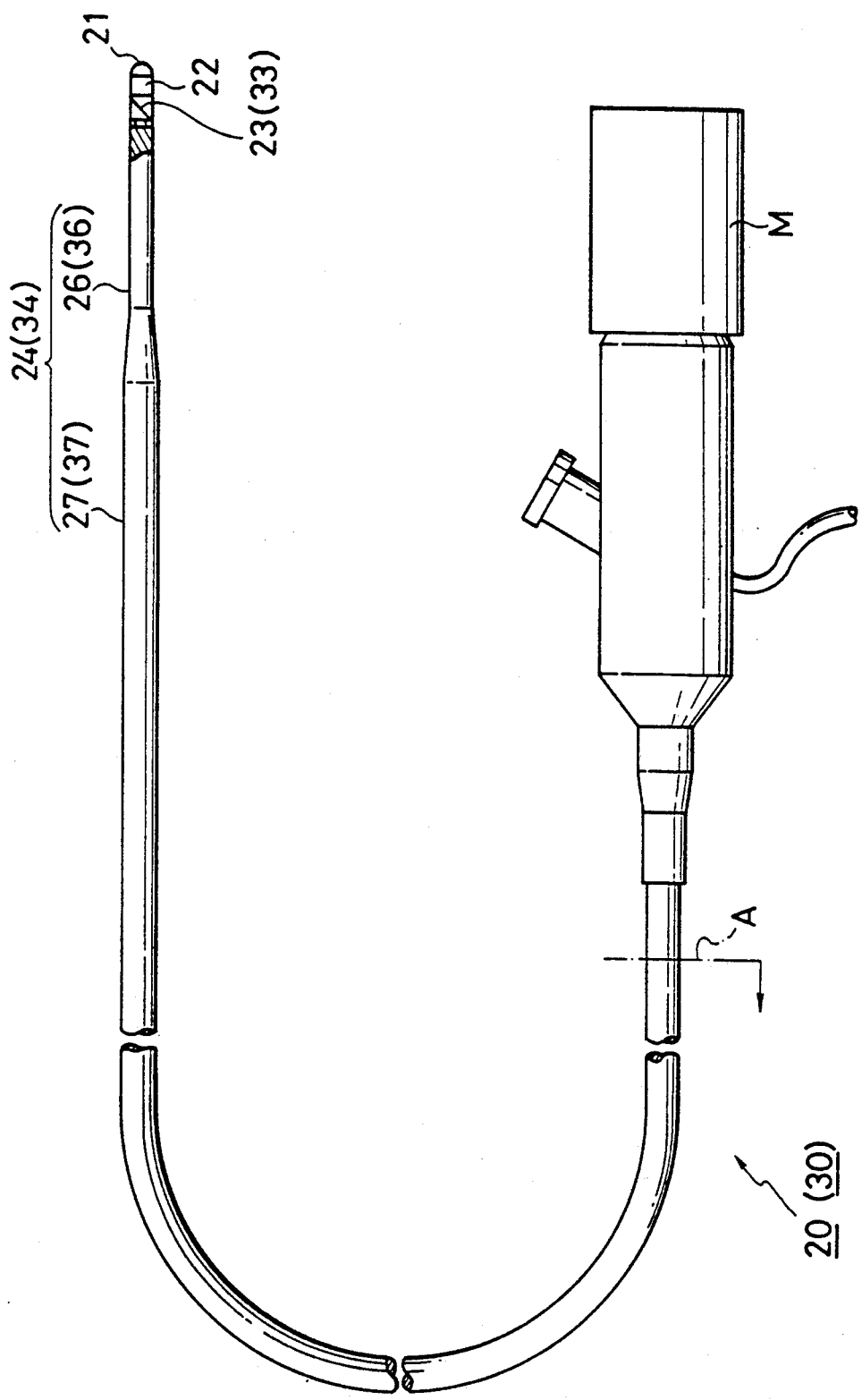
FIG. 4 is an elevational view of an ultrasonic probe according to the present invention.
Figure 5:
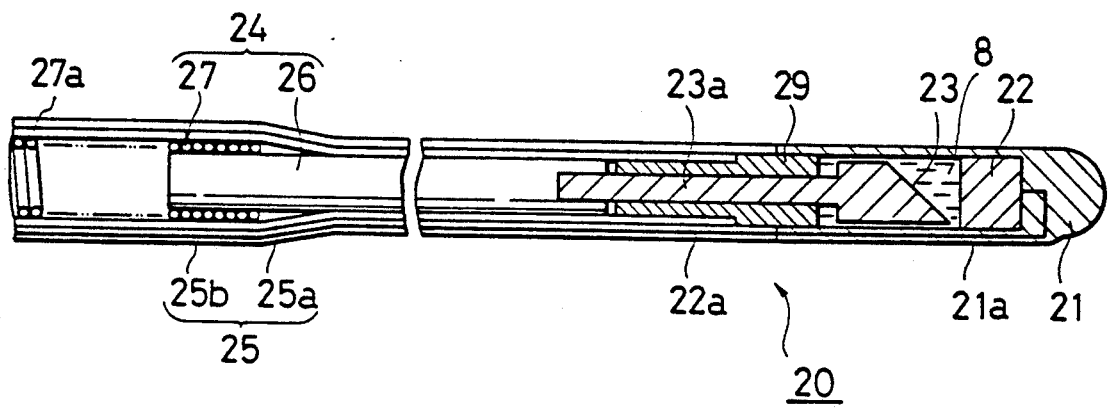
FIG. 5 is a fragmentary cross sectional view of a first embodiment of an ultrasonic probe according to the present invention.

Referring now to the drawings, wherein like reference characters designate like or corresponding components throughout the several views and thus the repeated description can be omitted for brevity, there is shown in FIGS. 4 and 5 a first embodiment of an ultrasonic probe 20 according to the present invention.

As shown in FIG. 4, in the ultrasonic probe 20, an oscillator 22 is mounted to a support member 21 positioned in one end of the probe 20, and a mirror 23 is arranged in opposition to the oscillator 22. A rotary transmission shaft 24 is composed of a small diameter shaft 26 connected to the mirror 23 and a large diameter rotary transmission shaft 27 which is connected with the small diameter shaft 26 and a drive motor M arranged in the other end of the probe 20. When the motor M is driven, a rotating force of the motor M is transmitted to the mirror through the rotary transmission shaft 24 while the rotary transmission shaft 24 is bent in any bending form. In this instance, the tip portion such as the support portion 21, the oscillator 22 and the mirror 23, and the rotary transmission shaft 24 from a part A to the tip portion of the probe 20 can be inserted into a narrow portion such as a blood vessel.

In FIG. 5, there is shown the tip portion of the probe 20 shown in FIG. 4. The oscillator 22 having a diameter of approximately 1 mm is mounted to the support member 21 having a round end, and the mirror 23 is arranged opposite to the oscillator 22 and is surrounded by an ultrasonic wave propagation material 8 such as water or a physiological saline solution. The support member 21 has an insertion entrance 21a. The mirror 23 integrally having a connection shaft 23a is coupled with the small diameter shaft 26 made of a steel wire having a diameter of approximately 0.5 mm and a length of several to 20 cm by fitting the end of the shaft 23a into a hollow formed one end of the small diameter shaft 26. The other end of the small diameter shaft 26 is connected to the large diameter flexible tubular rotary transmission shaft 27 having an outer diameter of approximately 2 to 3 mm, which is composed of a tubular coil or coil spring 27a made of a steel wire, by fitting the end of the small diameter shaft 26 into one end of the large diameter shaft 27. The large diameter transmission shaft 27 is also connected to the motor M. The connection shaft 23a of the mirror 23 is supported by a bearing 29 mounted on a covering tube 25. The convering tube 25 covers the bearing 29, the small diameter shaft 26 and the large diameter shaft 27.

The covering tube 25 is composed of an inner tube 25a and an outer tube 25b covering over the inner tube 25a. A signal cable 22a connected to the oscillator 22 passes through the insertion entrance 21a and the outer tube 25b. In this case, the small diameter tip portion of the probe 20 has a dimension such as an outer diameter of approximately less than 2 mm and a length of several to 20 cm.

Since the length of the ramus circumflexus $B_3$ or ramus descendens $B_4$ of a heart H of an adult is several cm, the length of the small diameter shaft 26 can be designed to a suitably minimum length corresponding to the length of the ramus circumflexus $B_3$ or ramus descendens $B_4$. Hence, even when this probe 20 is inserted into a bent blood vessel, only a small part of the tip portion of the probe 20 is given with a stress, and the rotating force of the motor M can be smoothly transmitted to the mirror 23 through the rotary transmission shaft 24 without causing an irregular rotation.

Since the large diameter flexible shaft 27 is composed of the tubular coil or coil spring 27a, when the probe 20 inserted in the blood vessel is largely bent, a compression or extension force caused in a side having small or large curvature can be effectively absorbed, and thus the rotating force of the motor M can be smoothly transmitted to the small diameter shaft and the mirror 23 through the large diameter shaft 27 without causing an uneven rotation.

Figure 1:
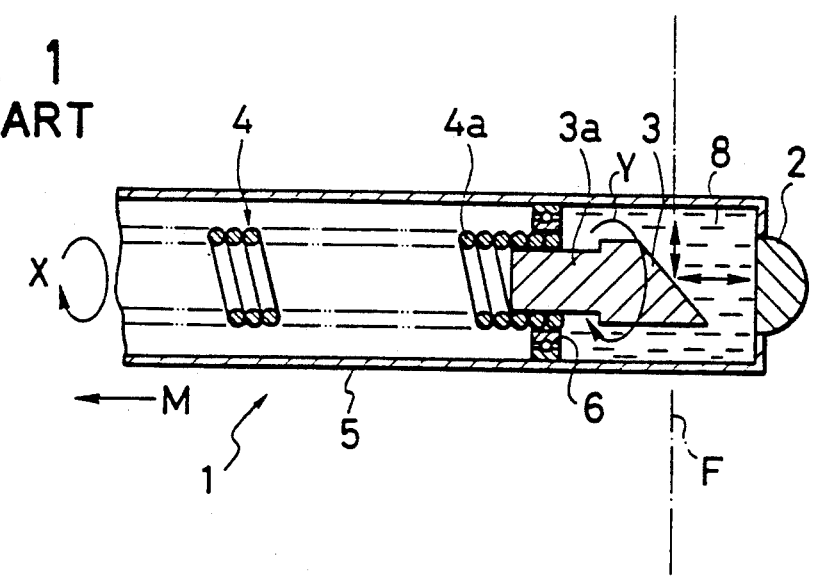
FIG. 1 is a fragmentary cross sectional view of a conventional ultrasonic probe.
Figure 2:
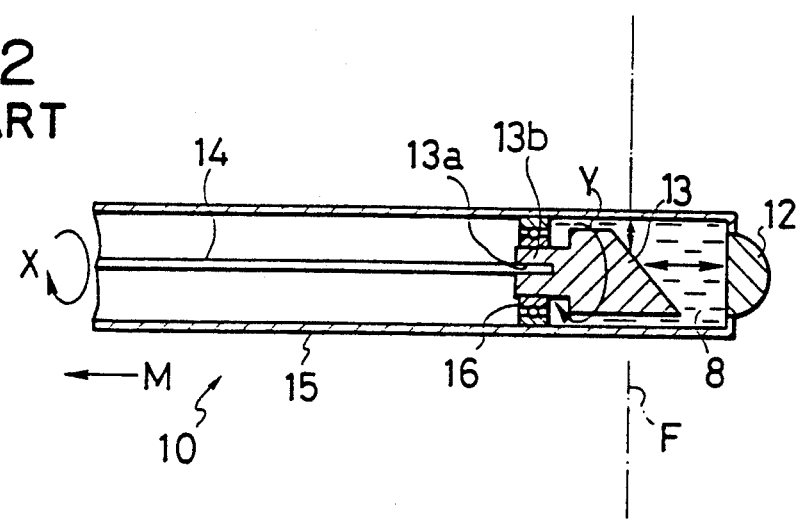
FIG. 2 ia a fragmentary cross sectional view of another conventional ultrasonic probe.
Figure 3:
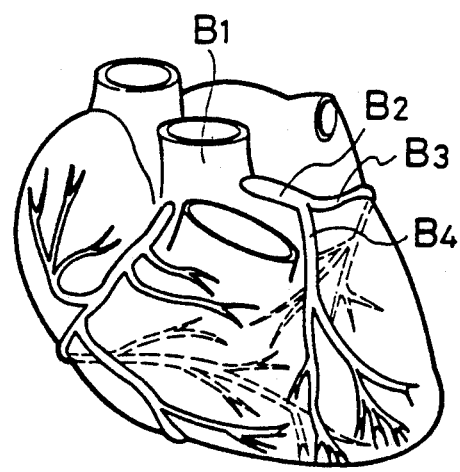
FIG. 3 is a perspective view of a heart.

Now, as shown in FIG. 3, when the probe 20 is inserted from its oscillator 22 into the ramus circumflexus $B_3$ or ramus descendens $B_4$ via the arotic arch (not shown), the aorta $B_1$ and the coronary artery $B_2$ of a heart H of an adult, the large diameter flexible shaft 27 is positioned extending in the arotic arch, the aorta $B_1$ and the coronary artery $B_2$, that is, a largely bent portion, and, since the small diameter shaft 26 has a proper length, the small diameter shaft 26 is positioned extending in the coronary artery $B_2$ and the ramus circumflexus $B_3$ or ramus descendens $B_4$, that is, a small bent portion.

Then, the motor M is driven in order to rotate the mirror 23, and an excitation pulse is sent to the oscillator 22 through the signal cable 22a. The oscillator 22 emits a ultrasonic wave to the mirror 23, and the mirror 23 can be smoothly rotated without causing an irregular rotation and reflect the ultrasonic wave to a right angle direction to transmit or receive the wave, thereby carrying out a ultrasonic wave scanning in a radial plane. The echo signals obtained by the scanning are fed to a ultrasonic diagnosis apparatus (not shown) through the signal cable 22a, in which a B-mode image in the radial plane around the ramus circumflexus $B_3$ or ramus descendens $B_4$ can be reproduced or displayed. Hence, a good ultrasonic wave image can be obtained.

Figure 6:
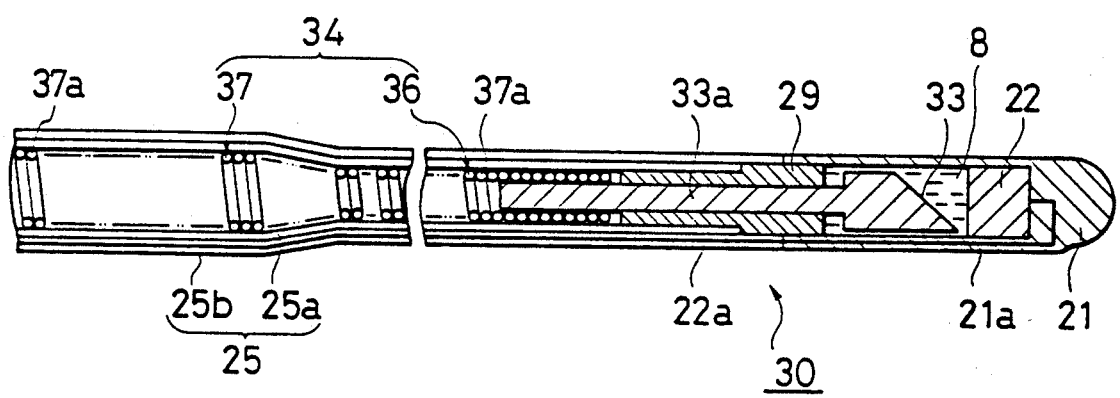
FIG. 6 is a fragmentary cross sectional view of a second embodiment of an ultrasonic probe according to the present invention.

In FIGS. 4 and 6, there is shown a second embodiment of a ultrasonic probe 30 according to the present invention. As shown in FIG. 4, the ultrasonic probe 30 having the same external appearance as the first embodiment shown in FIG. 5, includes a support member 21, an oscillator 22 mounted to the support member 21, a mirror 33 arranged in opposition to the oscillator 22 and a flexible rotary transmission shaft 34 composed of a small diameter shaft 36 and a large diameter shaft 37 coupled thereto.

As shown in FIG. 6, the probe 30 has a similar structure to the probe 20 shown in FIG. 5. In this embodiment, the mirror 33 is integrally formed with a connection shaft 33a. The flexible rotary transmission shaft 34 made of a tubular coil or coil spring 37a is composed of the small diameter flexible rotary transmission shaft 36 having an outer diameter of approximately 1 mm and a length of approximately 20 cm, and the large diameter flexible rotary transmission shaft 37 having an outer diameter of approximately 2 to 3 mm, the small diameter shaft 36 being integrally coupled to the large diameter shaft 37 by gradually enlarging its diameter. The end of the connection shaft 33a of the mirror 33 is fitted in one end of the small diameter shaft 36. The rotary transmission shaft 34 has the same function as the rotary transmission shaft 24 of the first embodiment shown in FIG. 5. In this instance, the probe 30 can be operated in the same manner as the probe 20 of the first embodiment, as described above. In this embodiment, the same effects and advantages of the first embodiment can be obtained.

Figure 7:
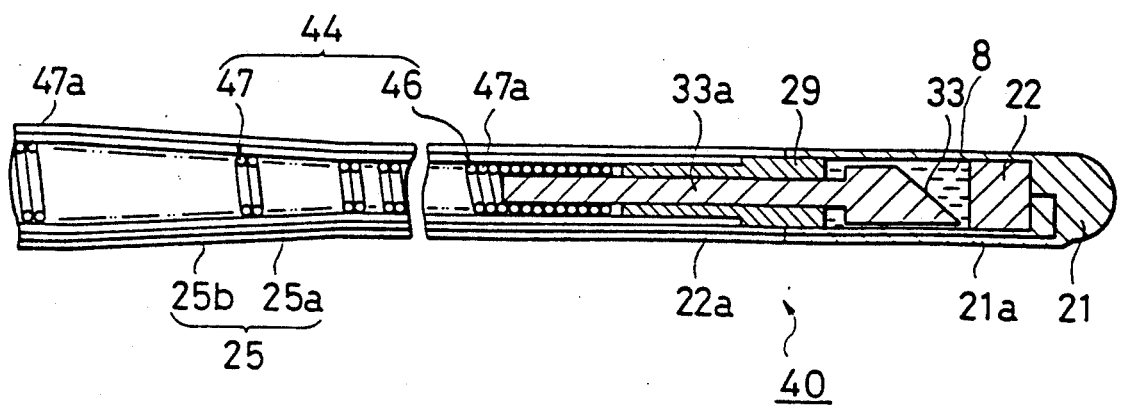
FIG. 7 is an fragmentary cross sectional view of a third embodiment of a ultrasonic probe according to the present invention.

In FIG. 7, there is shown a third embodiment of a ultrasonic probe 40 according to the present invention, having the same construction as the second embodiment shown in FIG. 6, except that a flexible rotary transmission shaft 44 made of a tubular coil or coil spring 47a is composed of a small diameter flexible rotary transmission shaft 46 and a large diameter flexible rotary transmission shaft 47, the small diameter shaft 46 being integrally coupled to the large diameter shaft 47 by more gradually enlarging its diameter than the rotary transmission shaft 34 of the second embodiment shown in FIG. 6. In this case, a more smooth surface of the coupling portion between the small and large diameter shafts 46 and 47 can be obtained to prevent an attachment of substances such as a thrombus to the surface of the rotary transmission shaft 44. In this instance, the probe 40 can be operated in the same manner as the probe 20 of the first embodiment, as described above. In this embodiment, the same effects and advantages of the above embodiments can be obtained.

Figure 8:
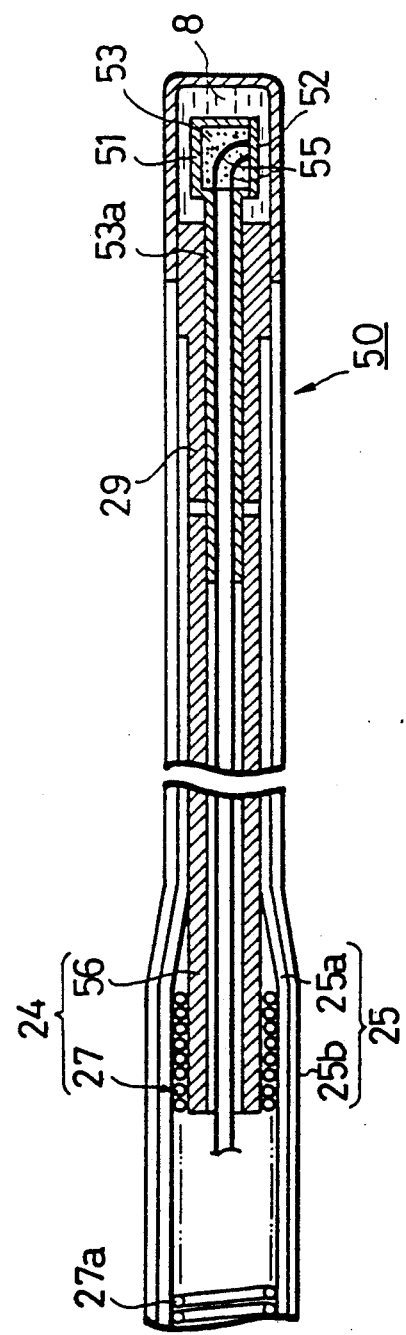
FIG. 8 is a fragmentary cross sectional view of a fourth embodiment of an ultrasonic probe according to the present invention.

In FIG. 8, there is shown a fourth embodiment of a ultrasonic probe 50 according to the present invention, having the same construction as the first embodiment shown in FIG. 5, except that a box member 51 is surrounded by the ultrasonic wave propagation material 8 and is connected to one end of a tubular connection shaft 53a instead of the mirror 23 in FIG. 5, and the other end of the tubular connection shaft 53a is coupled with one end of a small diameter tubular shaft 56. The box member 51 includes an oscillator 52 arranged in its one side, and a filler material 53 is packed within the box member 51. A couple of electric wires 55 is connected to the oscillator 52 and is passed through tubular holes of the tubular connection shaft 53a and the small diameter tubular shaft 56. In this case, the oscillator 52 facing a radial direction can be directly rotated to carry out the scanning. In this embodiment, the same effects and advantages of the first embodiment can be obtained.

From the above description, it is readily understood that the probe can be safely inserted from the oscillator into a fine portion such as a fine blood vessel, for example, the ramus circumflexus or ramus descendens, and the mirror or the oscillator can be rotated without causing an uneven or irregular rotation to obtain a good ultrasonic wave image.

Although the present invention has been described in its preferred embodiments with reference to the accompanying drawings, it it readily understood that the present invention is not restricted to the preferred embodiments and that various changes and modifications can be made by those skilled in the art without departing from the spirit and scope of the present invention.

What is claimed is:

1. A ultrasonic catheter probe adapted to be placed in a body vessel, comprising:
    a rotary transmission shaft comprising a first shaft portion and a second shaft portion at the distal tip of said probe, said first shaft portion having a bendable extent and greater flexibility than said second shaft portion, such that the first shaft portion can bend more easily than said second portion, said rotary transmission shaft being rotatable by a driver connected thereto;
    an oscillator arranged in opposition to one end of the transmission shaft for emitting an ultrasonic wave; and
    scanning means mounted to the one end of the rotary transmission shaft for reflecting the ultrasonic wave emitted by the oscillator to carry out an ultrasonic wave scanning, said first shaft portion having a first diameter, connected to the scanning means, said second shaft portion having a second diameter, connected to the driver, the first diameter being smaller than the second diameter.

2. The probe of claim 1, wherein the first diameter of the first shaft is approximately at most the same as that of the oscillator.

3. The probe of claim 1, wherein the scanning means comprises a mirror.

4. The probe of claim 1, wherein the oscillator has a diameter of approximately 1 mm.

5. The probe of claim 1, wherein the first diameter of the first shaft is approximately 0.5 mm.

6. The probe of claim 1, wherein the second shaft comprises a tubular coil having an outer diameter of approximately 2 to 3 mm.

7. The probe of claim 1, wherein the first shaft comprises a tubular coil having an outer diameter of approximately 1 mm.

8. The probe of claim 1, wherein the first shaft comprises a tubular coil integrally connected to the second shaft comprising a tubular coil through a connecting portion in which the diameter of the rotary transmission shaft smoothly varies from the first diameter to the second diameter.

9. The probe of claim 1, further comprising a covering tube for covering the rotary transmission shaft.

10. The probe of claim 9, wherein the rotary transmission shaft is supported by a bearing mounted on the covering tube.

11. A ultrasonic catheter probe adapted to be place in a body probe adapted to be placed in a body vessel, comprising:
    a rotary transmission shaft comprising a first shaft portion and a second shaft portion at the distal tip of said probe, said first shaft portion having bendable extent and greater flexibility than said second shaft portion, such that the first shaft portion can bend more easily than said second portion, said rotarty transmission shaft being rotatable by a driver connected thereto; and
    scanning means mounted to one end of the rotary transmission shaft for emitting an ultrasonic wave to carry out a ultrasonic wave scanning said first shaft portion having a first diameter, connected to the scanning means, said second shaft portion having a second diameter, connected to the driver, the first diameter being smaller than the second diameter.

12. The probe of claim 11, wherein the first diameter of the first shaft is approximately at most the same as that of the scanning means.

13. The probe of claim 11, wherein the scanning means comprises an oscillator.

14. The probe of claim 13, wherein the oscillator has a diameter of approximately 1 mm.

15. The probe of claim 11, wherein the first diameter of the first shaft is approximately 0.5 mm.

16. The probe of claim 11, wherein the second shaft comprises a tubular coil having an outer diameter of approximately 2 to 3 mm.

17. The probe of claim 11, wherein the first shaft comprises a tubular coil having an outer diameter of approximately 1 mm.

18. The probe of claim 11, wherein the first shaft comprises a tubular coil integrally connected to the second shaft comprises a tubular coil through a connecting portion in which the diameter of the rotary transmission shaft smoothly varies from the first diameter to the second diameter.

19. The probe of claim 11, further comprising a covering tube for covering the rotary transmission shaft.

20. The probe of claim 19, wherein the rotary transmission shaft is supported by a bearing mounted on the covering tube.

* * * * *